United States Patent [19]

Endo et al.

[11] Patent Number: 5,149,641
[45] Date of Patent: Sep. 22, 1992

[54] PROCESS FOR PRODUCING MEVALONIC ACID

[75] Inventors: Akira Endo; Seiji Koike, both of Tokyo, Japan

[73] Assignee: Asahi Denka Kogyo Kabushiki Kaisha, Tokyo, Japan

[21] Appl. No.: 629,184

[22] Filed: Dec. 17, 1990

Related U.S. Application Data

[63] Continuation of Ser. No. 158,314, Feb. 22, 1988, abandoned.

[30] Foreign Application Priority Data

| Mar. 4, 1987 | [JP] | Japan | 62-49620 |
| Mar. 4, 1987 | [JP] | Japan | 62-49621 |
| Mar. 4, 1987 | [JP] | Japan | 62-49622 |
| Mar. 4, 1987 | [JP] | Japan | 62-49623 |

[51] Int. Cl.$^5$ .................. C12P 17/06; C12P 7/46; C12P 7/40; C12N 1/16
[52] U.S. Cl. .................. 435/125; 435/145; 435/136; 435/255; 435/911; 435/244; 435/254
[58] Field of Search ............... 435/125, 145, 136, 911, 435/254, 244, 255

[56] References Cited

U.S. PATENT DOCUMENTS 3,617,447 11/1917 Arima .................. 435/136

FOREIGN PATENT DOCUMENTS 0098473 1/1984 European Pat. Off. .

OTHER PUBLICATIONS

Tamura et al., *Appl. Microbiol.* 16, pp. 965–967, 1968.
Demain, D. L. In *Biosynthesis of Antibiotics* vol. I, 1966, pp. 37–39, Academic Press.
N. J. W. Kreger-van Rij, *The Yeasts, A Taxonomic Study*, Third Revised and Enlarged Edition, Elsevier Science Publishers B. V., Amsterdam, 1984, pp. 399–407.

*Primary Examiner*—Irene Marx
*Attorney, Agent, or Firm*—Young & Thompson

[57] ABSTRACT

According to the present invention, mevalonic acid can be produced in such a high yield as to be available on an industrial scale by culturing specified microorganism(s) such as *Saccharomycopsis fibuligera* IFO 0107 and then collecting mevalonic acid from the culture medium.

2 Claims, 1 Drawing Sheet

PROCESS FOR PRODUCING MEVALONIC ACID

This application is a continuation, of application Ser. No. 158,314, filed Feb. 22, 1988 now abandoned.

BACKGROUND OF THE INVENTION

1. Field of the Invention

This invention relates to a process for producing mevalonic acid. More particularly, it relates to a process for producing mevalonic acid in a high yield.

It is wellknown that mevalonic acid has two structures, i.e., acid- and lactone-forms and that these forms can be converted into each other. Thus the term "mevalonic acid" as used herein involves these two forms, unless otherwise noted.

2. Description of the Prior Art

Mevalonic acid, which was isolated by Wright et al. for the first time (cf. JACS. 78, 5273 (1956)), is known as an important intermediate in the synthesis of various isoprenoids including cholesterol.

Mevalonic acid is further employed as a growth promotor for microorganisms and plants, since it exerts important effects of, for example, promoting the growth of various microorganisms and plants. It is furthermore employed as a precursor for pyrethroid pesticides, ubiquinone (respi-coenzyme Q), dolichol (glycoprotein synthesizing factor) and fat soluble vitamines.

Since natural mevalonic acid is scarcely available, synthetic racemates thereof have been employed in conventional studies.

Known processes for producing natural mevalonic acid include those described in Applied Microbiol., 16, 965 (1968) and U.S. Pat. No. 3,617,447 wherein *Saccharomycopsis fibuligera* NRRL Y-7069 (IAM-4347) is employed. However these processes can give only limited yields, i.e., 700 to 1000 $\mu$g/ml and thus the application thereof on an industrial scale has not been achieved yet.

SUMMARY OF THE INVENTION

It is an object of the present invention to provide a process for producing mevalonic acid in such a high yield as to be available on an industrial scale.

According to the present invention, the above object can be achieved by using specified microorganisms.

More particularly, the process for producing mevalonic acid of the present invention essentially comprises culturing one or more microorganisms selected from among *Saccharomycopsis fibuligera* IFO 0107, IFO 0103, IFO 0104, IFO 0105, IFO 0106, IFO 0109, IFO 0111, IFO 1665, IFO 1711, IFO 1745, AHU 4113, IAM 4247, OUT 6071, HUT 7234, ATCC 2080, ATCC 2082, ATCC 2088, ATCC 20145, ATCC 24945, ATCC 44872, ATCC 46252, ATCC 46253, ATCC 46949, ATCC 52921, NRRL Y-1060, NRRL Y-1064, NRRL Y-2385, NRRL Y-7061, NRRL Y-7221, NRRL Y-7324, NRRL Y-7464, DSM 70554, CBS 2524, CBS 2527, CBS 2551, CBS 2553, CBS 5158, CBS 5190, CBS 5843, CBS 6338, CBS 6860 and variants thereof, preferably IFO 0107, in a medium and then collecting mevalonic acid from the culture medium.

The abbreviations as used above, i.e., IFO, ATCC, NRRL, DSM, CBS, AHU, IAM, OUT and HUT represent strains deposited with Institute for Fermentation. Osaka; American Type Culture Collection; ARS Northern Regional Research Center; Deutsche Sammlung von Mikroorganismen; Centraalbureau voor Schimmelcultures, Fact. of Agr., Hokkaido Univ.; Inst. of Appl. Microbiol., Tokyo Univ.; Dept. of Fermentation, Fact. of Tech., Osaka Univ.; and Dept. of Fermentation, Fact. of Tech., Hiroshima Univ., respectively.

DETAILED DESCRIPTION OF THE INVENTION

Figure 1:
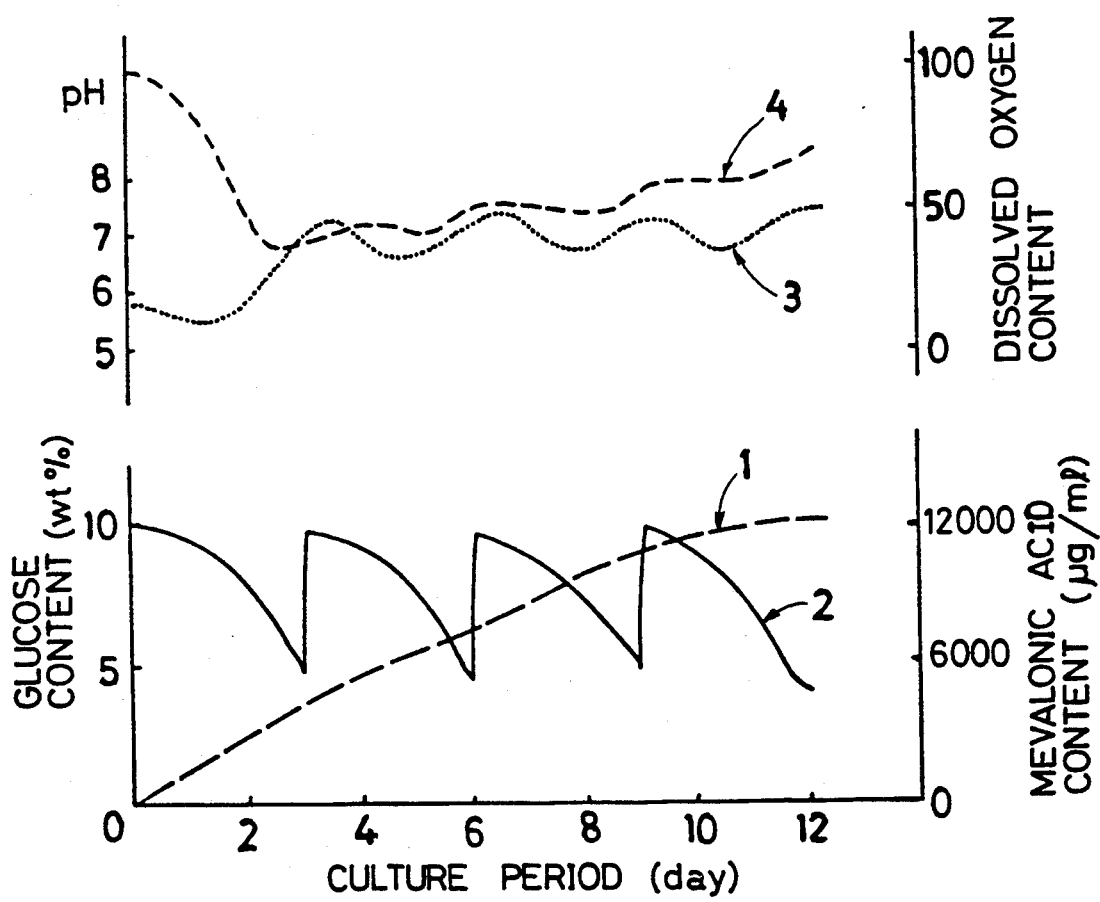
FIG. 1 shows graphs indicating relationships between the culture period, on one hand, and the dissolved oxygen content, wherein "100" means saturation at starting period. pH value, glucose content (% by weight) and mevalonic acid content ($\mu$g/ml), on the other hand, wherein 1 refers to the content of mevalonic acid; 2 to the content of glucose; 3 to the pH value; and 4 to the content of dissolved oxygen.

The process of the present invention for producing mevalonic acid with the use of the abovementioned microorganism(s) may be carried out in a conventional manner, e.g., according to the one disclosed in U.S. Pat. No. 3,617,447. However it is preferably carried out in the following manner.

Microorganism(s) are inoculated into a medium containing a carbon source, an organic nitrogen source, nonionic surfactant(s) capable of solubilizing cell membrane and inorganic salt(s) each of a given concentration and then cultured therein under shaking at 20° to 40° C. preferably 25° to 35° C.; or under aeration/agitation at 100 to 500 rpm, preferably 200 to 400 rpm, and 0.1 to 1.5 VVM, preferably 0.5 to 1.0 VVM for a given period. Then the concentration of the carbon source, dissolved oxygen or the pH value thereof is determined and the substrate(s) are added to the medium, if required. After repeating the above procedure several times, the culture is completed when no mevalonic acid is produced any more. After the completion of the culture, the cells are removed from the medium in a conventional manner such as centrifugation or filtration. Then the supernatant is subjected to conventional purification technique(s), for example, concetration by reverse osmosis or distillation in vacuo; countercurrent distribution with the use of butanol or ethyl acetate; column chromatography with the use of, for example, silica gel, palar characteristics gel or an ion exchange resin; reduced pressure or molecular distillation; or crystallization to thereby give the aimed mevalonic acid.

In the process of the present invention, the medium may further contain some additives such as a defoaming agent without departing from the spirit and scope of the invention. The concentration of the carbon source in the culture liquor may be determined by, for example, an enzymatic method with the use of glucose oxidase. The term "culture liquor" as used herein means a solution obtained by removing the cells from the culture medium by, for example, centrifugation or filtration.

The medium to be used in the present invention may comprise, for example, 2 to 15% by weight of a carbon source, 0.5 to 3% by weight of an organic nitrogen source, 0.02 to 0.1% by weight of a surfactant and the balance of water. It may further contain, for example, 0.01 to 5% by weight portions of inorganic salt(s) such as phosphates, potassium salts, magnesium salts or calcium salts.

In the present invention, it is preferable that the substrate is added to the medium in such a manner as to give the concentration of the carbon source in the culture liquor of 2 to 15% by weight, preferably 5 to 10% by weight. However it is preferable that the substrate is added to the culture medium while measuring the pH value thereof or the amount of dissolved oxygen therein as an indication, since generally it takes a long period of time to determine the concentration of the carbon source.

When the pH value is employed as the indication, the substrate may be added when the pH value exceeds 7. On the other hand, when the dissolved oxygen is employed as the indication, the substrate may be added as soon as the content of the dissolved oxygen has passed a minimum point in the curve of FIG. 1 in which the initial value refers to the saturation, namely, when the content begins to rise again after it has fallen.

The amount of the substrate to be added at this point depends on the carbon source concentration at the addition point which should be determined preliminarily.

The composition of the substrate to be added may be either the same as or different from that of the medium prior to the culture, so long as it contains a carbon source. Preferable examples thereof include glucose, fructose, maltose, malt extract, glycerol and acetates. Although the substrate may be in any form so long as it is a aseptic one, it is preferably in the form of an aqueous solution which can be readily sterilized. It is preferable that the aqueous solution has a high concentration of, for example, 40% or higher, though it is not restricted thereby.

In the present invention, it is preferable to add one or more nonionic surfactants capable of solubilizing cell membrane selected from among, for example, polyoxyethylene glycol p-t-octylphenyl ether known as Triton ® and Nonidet ®; polyoxyethylene glycol alkyl ethers known as Brij ® and Emulgen ®; and polyoxyethylene glycol sorbitan ester known as Tween ® and Span ® to the medium. Particular examples thereof include Triton ® X-100, Triton ® X-114, Triton ® X-102, Nonidet ® P-40, Brij ® 35, Brij ® 76, Brij ® 96, Brij ® 56, Emulgen ® 120, Emulgen ® 109 P, Tween ® 20 and Span ® 20. Among these surfactants, Triton ® X-100 is particularly preferable and the yield of mevalonic acid can be further elevated by adding the same in an amount of 0.002 to 0.2% by weight, preferably 0.02 to 0.1% by weight, based on the medium. This is because the surfactant solubilizes the cell membrane of each microorganism and accerelates the liberation of mevalonic acid from the cell, thus elevating the yield of the mevalonic acid.

It is preferable that not inorganic nitrogen sources but organic one(s) such as peptone, yeast extract, meat extract, casein corn steep liquor or soybean meal are exclusively employed as the nitrogen source from the viewpoint of increasing the yield.

According to the process for producing mevalonic acid of the present invention, mevalonic acid can be produced in such a high yield as to be available on an industrial scale.

To further illustrate the present invention, and not by way of limitation, the following Examples will be given.

In the following Examples and comparative Examples, mevalonic acid was determined in the following manner.

Determination of Mevalonic Acid 0.8 ml of a sample solution is introduced into a Spitch tube and the pH value thereof is adjusted to 2 with a 1N HCl solution. The 1 g of anhydrous $Na_2SO_4$ is added thereto followed by 2.0 ml of ethyl acetate and the resulting mixture is stirred. After removing the upper phase, 2.0 ml of ethyl acetate is further added to the lower phase followed by stirring. The upper phase is taken up and combined with the former one. This procedure is repeated twice to thereby give 6.0 ml of an ethyl acetate phase in total. Then the ethyl acetate phase is evaporated to dryness and the obtained dry matter is quantatively determined by gas chromatography with the use of 3,4-dimethoxybenzaldehyde as an internal standard. The gas chromatography is carried out under the following conditions:

column size: 3 mm in diameter and 1000 mm in length (stainless);
column liquid phase: 10% Thermon-3000;
column support: Chromosorb W AW-DMCS, 80-100 mesh;
column temperature: 180° C.;
injection temperature: 230° C.; and
carrier gas: $N_2$ (40 ml/min).

EXAMPLE 1

A medium comprising 10% by weight of glucose, 1% by weight of malt extract, 0.5% by weight of peptone, 0.1% by weight of yeast extract, 0.3% by weight of $KH_2PO_4$, 0.05% by weight of $MgSO_4 \cdot 7H_2O$, 1% by weight of $CaCO_3$, 0.05% by weight of Triton ® X-100 and the balance of water was prepared. 200 ml of this medium was inoculated with one platinum loopful of *Saccharomycopsis fibuligera* IFO 0107, which was then cultured therein at 28° C. under shaking for three days. Then the microorganisum was inoculated into 20 l of the same medium and cultured therein at 28° C. under aeration/agitation at 300 rpm and 20 l/min while determining the glucose concentration, pH value and the content of dissolved oxygen.

On the third day of the culture, glucose in the culture liquor was determined. After confirming that the glucose concentration fell below 5%, 2.0 kg of a 50% by weight aqueous solution of glucose was added thereto and the culture was continued. On the sixth and ninth days, 2.0 kg portions of the 50% by weight aqueous solution of glucose were further added and the culture was carried out for 12 days in total. After the completion of the culture, mevalonic acid contained from the culture medium was determined in the abovementioned manner. Thus 12100 μg/ml of mevalonic acid was obtained.

FIG. 1 shows graphs indicating relationships between the culture period, on one hand, and the dissolved oxygen content, wherein "100" means the saturation, pH value, glucose content (% by weight) and mevalonic acid content (% by weight). These curves suggest that when the glucose content in the culture liquor fell below 5% on the third day of the culture, the pH value exceeded 7 and the dissolved oxygen content passed the minimum.

EXAMPLE 2

The same medium as the one described in Example 1 was prepared except that the Triton ® X-100 was replaced with 0.3% by weight of ammonium chloride. Then the culture was carried out in the same manner as the one described in Example 1 for 12 days. As a result, 6600 μg/ml of mevalonic acid was obtained.

EXAMPLE 3

A medium comprising 10% by weight of glucose, 1% by weight of malt extract, 0.5% by weight of peptone, 0.1% by weight of yeast extract, 0.3% by weight of $KH_2PO_4$, 0.05% by weight of $MgSO_4$ $7H_2O$. 1% by weight of $CaCO_3$, 0.05% by weight of Triton ® X-100, 0.3% by weight of ammonium chloride and the balance of water was prepared. 200 ml of this medium was inoculated with one platinum loopful of *Saccharomycopsis fibuligera* IFO 0107, which was then cultured therein at 28° C. under shaking for three days. Then the microorganism was inoculated into 20 l of the same medium and cultured therein at 28° C. under aeration/agitation at 300 rpm and 20 l/min.

After effecting the culture for six days, 4200 μg/ml of mevalonic acid was obtained.

EXAMPLES 4 and 5

The culture of Example 3 was followed except that the medium contained neither Triton ® X-100 nor ammonium chloride (Example 4). After effecting the culture for six days, 3900 g/ml of mevalonic acid was obtained.

Separately the culture of example 3 was followed except that the medium contained no Triton ® X-100 (Example 5). After effecting the culture for six days. 3010 μg/ml of mevalonic acid was obtained.

Comparative Examples 1 and 2

The procedure of Example 5 was followed except that the *Saccharomycopsis fibuligera* IFO 0107 was replaced with *Saccharomycopsis fibuligera* IFO 1714 (Comparative Example 1) or NRRL Y-7069 (IAM-4347) (Comparative Example 2). After effecting the culture for six days, the yields of mevalonic acid in these cases were 910 μg/ml and 780 μg/ml, respectively.

EXAMPLE 6

10 ml of the medium as described in Example 1 was introduced into a test tube and sterilized at 121° C. for 15 minutes. Then it was inoculated with one platinum loopful of each strain of *Saccharomycopsis fibuligera* as shown in Table 1, which was then cultured therein under shaking at 250 rpm at 28° C. On the fourth and eighth days of the culture, 1.0 g portions of a 50% by weight aqueous solution of glucose were added thereto. After effecting the culture under shaking for 12 days, the culture medium was centrifuged at 2500 rpm for ten minutes and mevalonic acid in the filtrate was determined. Table 1 shows the yields of mevalonic acid thus obtained.

TABLE 1

| *Saccharomycopsis fibuligera* strain | | Mevalonic acid (μg/ml) |
| --- | --- | --- |
| IFO | 0103 | 3970 |
| IFO | 0104 | 6020 |
| IFO | 0105 | 9640 |
| IFO | 0106 | 5020 |
| IFO | 0109 | 7000 |
| IFO | 0111 | 7980 |
| IFO | 1665 | 8360 |
| IFO | 1711 | 4170 |
| IFO | 1745 | 9740 |
| AHU | 4113 | 4190 |
| IAM | 4247 | 9170 |
| OUT | 6071 | 5660 |
| HUT | 7234 | 3650 |
| ATCC | 2080 | 5630 |
| ATCC | 2082 | 4140 |
| ATCC | 2088 | 5110 |
| ATCC | 20145 | 5860 |
| ATCC | 24945 | 6650 |
| ATCC | 44872 | 5160 |
| ATCC | 46252 | 8540 |
| ATCC | 46253 | 3830 |
| ATCC | 46949 | 5500 |
| ATCC | 52921 | 9220 |
| NRRL | Y-1060 | 7170 |
| NRRL | Y-1064 | 3900 |
| NRRL | Y-2385 | 4880 |
| NRRL | Y-7061 | 5900 |
| NRRL | Y-7221 | 3200 |
| NRRL | Y-7324 | 8680 |
| NRRL | Y-7464 | 4290 |
| DSM | 70554 | 5470 |
| CBS | 2524 | 7890 |
| CBS | 2527 | 6030 |
| CBS | 2551 | 4960 |
| CBS | 2553 | 7400 |
| CBS | 5158 | 6510 |
| CBS | 5190 | 5290 |
| CBS | 5843 | 5440 |
| CBS | 6338 | 8220 |
| CBS | 6860 | 3530 |

EXAMPLE 7

22 l of the culture medium as obtained in Example 1 was centrifuged at 5000 rpm to thereby give 15 l of a filtrate. This filtrate was concentrated to 5 l with the use of a reverse osmosis membrane, adjusted to a pH value of 2 with a 50% by weight aqueous solution of phosphoric acid and then extracted thrice with 5 l portions of ethyl acetate. Thus 15 l of an ethyl acetate phase was obtained. This phase was re-extracted with 5 l of a 0.02N aqueous solution of sodium hydroxide, and aqueous phase was adjusted to a pH value of 2 with a 50% by weight aqueous solution of phosphoric acid and then passed through a DIAION HP-20 ® column (1 l). The effluent was extracted with 5 l portions of ethyl acetate thrice to thereby give 15 l of an ethyl acetate phase, which was then dehydrated over anhydrous sodium sulfate and evaporated to dryness. The obtained dry matter was dissolved in a small amount of an acetone/benzene mixture (1/7) and separated by means of silica gel (1500 g) (WAKOGEL ® C-200) column chromatography. Then the fraction containing mevalonic acid was dried to give 91.4 g of an oily product.

specific rotation $[\alpha]_D^{25} = -22.0°$ (C=3.20 in ethanol).

What is claimed is:

1. A process for producing mevalonic acid, which comprises culturing a strain having all of the identifying characteristics of *Saccharomycopsis fibuligera* IFO 0107 in an aqueous nutrient medium containing assimilable sources of carbon, nitrogen and inorganic substances, wherein an effective amount of a non-ionic surfactant is added to the medium during the culturing period and thereafter recovering mevalonic acid from the culture medium.

2. A process for producing mevalonic acid as set forth in claim 1, wherein said assimilable sources of carbon are added to the medium one or more times during the culturing period, and wherein said nitrogen source is organic nitrogen.

* * * * *